| United States Patent [19] | [11] Patent Number: 4,806,686 |
| Ernst et al. | [45] Date of Patent: Feb. 21, 1989 |

[54] PREPARATION OF RIBITYLXYLIDINE

[75] Inventors: Hansgeorg Ernst, Ludwigshafen; Hartmut Leininger, Greenaa, Denmark; Joachim Paust, Neuhofen, Fed. Rep. of Germany

[73] Assignee: BASF Aktiengesellschaft, Ludwigshafen, Fed. Rep. of Germany

[21] Appl. No.: 42,823

[22] Filed: Apr. 27, 1987

[30] Foreign Application Priority Data

May 10, 1986 [DE] Fed. Rep. of Germany ....... 3615834

[51] Int. Cl.$^4$ .............................................. C07C 85/02
[52] U.S. Cl. .................... 564/398; 564/399; 564/413
[58] Field of Search ................. 564/398, 399, 413

[56] References Cited

U.S. PATENT DOCUMENTS

| 2,429,244 | 10/1947 | Spiegelberger | 536/18.7 |
| 2,477,560 | 2/1946 | Flexser et al. | 536/55.3 |
| 4,360,669 | 11/1982 | Schmidt et al. | 544/251 |
| 4,567,262 | 1/1986 | Grimmer et al. | 544/251 |
| 4,602,086 | 7/1986 | Hiroshi et al. | 536/125 |
| 4,673,742 | 6/1987 | Grimmer et al. | 544/251 |
| 4,687,847 | 8/1987 | Grimmer et al. | 544/251 |

FOREIGN PATENT DOCUMENTS

| 46495 | 7/1981 | European Pat. Off. |
| 2923268 | 12/1980 | Fed. Rep. of Germany |
| 3437571 | 6/1985 | Fed. Rep. of Germany |

*Primary Examiner*—Glennon M. Hollrah
*Assistant Examiner*—John A. Sopp
*Attorney, Agent, or Firm*—Oblon, Fisher, Spivak, McClelland & Maier

[57] ABSTRACT

N-(D)-ribitylxylidine (I) is prepared by reacting (D)-ribose (II) with 3,4-dimethylaniline (III) or 3,4-dimethyl-1-nitrobenzene (IV) in aqueous or aqueous/organic solution or in solution in a water-soluble organic solvent under an elevated hydrogen pressure and in the presence of a hydrogenation catalyst and of a boric acid compound, (a) using the boric acid compound in a catalytic amount of from about 6 to 35 mmol, preferably from 6 to 20 mmol, per mol of ribose,
(b) carrying out the reaction under a hydrogen pressure of from 1 to 20, preferably from 2 to 9, bar and
(c) carrying out the hydrogenation at from 40° to 80° C. over Raney nickel as hydrogenation catalyst.

6 Claims, No Drawings

PREPARATION OF RIBITYLXYLIDINE

The present invention relates to a process for preparing N-(3,4-dimethylphenyl)-D-1-ribitylamine (ribitylxylidine; I) by reacting (D) ribose with 3,4-dimethylaniline at elevated temperatures and under hydrogenating conditions. I is an important intermediate in the industrial production of riboflavin (vitamin B₂).

I is obtained by reductive amination of D-ribose (II) with 3,4-dimethylaniline (III) or 3,4-dimethylnitrobenzene (IV) (cf. Ullmann's Encyklopädie der technischen Chemie, 4th edition, volume 23 (1983), pp. 666/67).

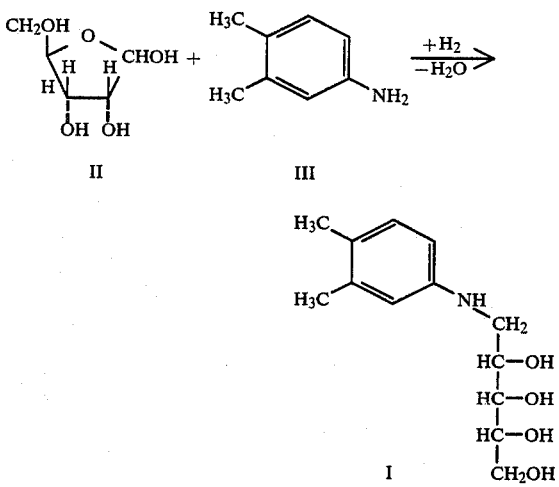

In industry, this reductive condensation is carried out as a catalyst hydrogenation.

The direct reaction of II with III in the presence of H₂ and Raney nickel to give I without isolation of the intermediate riboside V

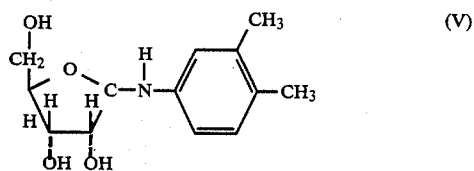

is described in U.S. Pat. No. 2,477,560. The disadvantage with this process is that hydrogen pressures of from about 25 to 50 bar are necessary to obtain high yields.

U.S. Pat. No. 2,429,244 discloses a process for preparing I in which not only only crystalline ribose but also solutions of crude ribose can be used. In this process, the D-ribose solution is treated with not less than 1 mole of boric acid and 1 mole of 3,4-dimethylaniline per mole of ribose, and the resulting intermediate, which contains crystalline boric acid, is separated off and washed and then catalytically hydrogenated in alkanolic solution. With this process, too, relative high hydrogen pressures are necessary. The ribitylxylidine yields range from about 75 to 78% of theory.

In EP No. 46,495, I is likewise obtained by reacting crude ribose with 3,4-dimethylaniline and equimolar amounts of boric acid in aqueous or aqueous/organic solution, isolating the resulting crystalline borate and subsequently hydrogenating this borate in aqueous or aqueous-organic solution at from 20° to 70° C. under a hydrogen pressure of from 10 to 100 bar, preferably at 30 bar, in the presence of a hydrogenation catalyst. The yield is around 85.5%, based on ribose. The disadvantages here are again the high hydrogen pressures as well as the use of equimolar amounts of boric acid with its attendant workup problems.

Furthermore, German Laid-Open Applications DOS No. 3,004,304 and DOS No. 2,923,268 disclose the following way of preparing I. Epimerization of D-arabinose with molybdenum(VI) compounds and subsequent coarse removal of unconverted arabinose by crystallization gives a crude ribose which, under a hydrogen pressure of 3 bar, can be reacted over Pd/C in place of Raney nickel as hydrogenation catalyst with 3,4-dimethylaniline or with 3,4-dimethynitrobenzene, which is reduced in situ to 3,4-dimethylaniline, to give I. However, the yields of I in this process are only around 78.5%.

According to German Laid-Open Application DOS No. 3,437,571, the above-described epimerization of D-arabinose with molybdenum(VI) compounds is possible with a far higher degree of epimerization if the epimerization is carried out in the presence of a boric acid compound. In this process, the boric acid compound is used in an amount which corresponds to not less than 0.5 times or preferably 1.5 times the molar amount of D-arabinose, and, after the epimerization, is generally removed by precipitation with methanol, by electric dialysis and/or by treating the solution with a weakly basic ion exchanger resin. Subsequently the ribose is reacted in this process with 3,4-dimethylaniline under high hydrogen pressures (40–50 bar) to give I.

It is an object of the present invention to improve the preparation of I by hydrogenative condensation of II with III or IV in such a way as to produce I, despite employing only a low hydrogen pressure, in a high yield in as simple a manner as possible.

We have found that this object is achieved, surprisingly, and that I is obtained in a very high yield of from 87 to over 90% of theory, based on ribose, on reacting II with III or IV in aqueous or organic/aqueous solution in the presence of hydrogen and, if Raney nickel is used as the catalyst, a hydrogenation catalyst even under a low hydrogen pressure if the reaction is carried out in the presence of a catalytic amount of a suitable boric acid compound.

The present invention accordingly provides a process for preparing N-(D)-ribitylxylidine (I) by reacting (D)-ribose (II) with 3,4-dimethylaniline (III) or 3,4-dimethyl-1-nitrobenzene (IV) in aqueous or aqueous/organic solution or in solution in a water-soluble organic solvent under an elevated hydrogen pressure and in the presence of a hydrogenation catalyst and of a suitable boric acid compound, which comprises (a) using the boric acid compound in a catalytic amount of from about 6 to 35 mmol, preferably from 6 to 20 mmol, per mol of ribose, (b) carrying out the reaction under a hydrogen pressure of from 1 to 20, preferably from 2 to 9, bar and (c) carrying out the hydrogenation at from 40° to 80° C., preferably from 50° to 60° C., over Raney nickel as hydrogenation catalyst.

Suitable boric acid compounds are boron oxide, borates or boric acid itself.

Reducing the hydrogen pressure appreciably reduces the investment expense for the hydrogenation plant and the level of technical complexity.

Adding the boric acid catalyst increases the ribitylxylidine yields, as the Examples show, by from 25 to 40% of theory (depending on starting material). This effect is observed with any grade of ribose. The requisite amount of catalyst varies from about 6 to 35 mmol per mol of ribose. The exact amount depends on the grade of ribose used in a specific case, and can be determined in simple preliminary experiments.

The reaction according to the invention is in general carried out in one of the lower alcohols suitable for this reaction, in particular methanol, in the pure form or even in the presence of water. The reaction temperatures range from 40° to 80° C., in particularly from 50° to 60° C. The hydrogen pressure range for the reaction generally extends from 1 to 20 bar. Advantageously the hydrogen pressure is within the range from 2 to 9 bar, in particular from 2 to 5 bar, which is feasible in existing reactors, since customary reactors are generally sanctioned for reactions under a pressure of up to 10 bar. The preferred pressure range makes it possible to dispense with the use of compressors and to charge the reactor from hydrogen cylinders. In principle, the reaction could even be carried out under atmospheric pressure, but in that case a slightly more contaminated ribamine is obtained, so that a small $H_2$ overpressure is preferable. The reaction takes from about 4 to 6 hours. On completion of the reaction, the Raney nickel is filtered off, the filtrate is concentrated, and the ribitylxylidine is precipitated therefrom in high yield and purity by adding water.

If 3,4-dimethyl-1-nitrobenzene is used as starting material for the reaction according to the invention, it is advisable to hydrogenate it first to 3,4-dimethylaniline in the same solvent and over the same hydrogention catalyst. This version of the process is illustrated Example 16.

The process according to the invention produces the important intermediate ribitylxylidine for the industrial production of riboflavin in a simple manner and in a very high yield even when Raney nickel and a low hydrogen pressure are employed.

EXAMPLES

General method

In each case the amount of 3,4-dimethylaniline (III) shown in the following Tables was dissolved in 150 ml of methanol, 20 g of water-moist Raney nickel were added, and the resulting mixture was heated in an autoclave to about 55° C. The methanolic ribose (II) solution defined in more detail in the Tables below and in some cases containing a catalytic amount of boric acid was then pumped in over 4 hours (h). Residues were then flushed in with 60 ml of methanol, and the reaction mixture was subsequently reacted at 5 bar hydrogen pressure and 55° C. for a further 2 h. The reaction mixture was then filtered hot from the catalyst, and the filter was washed with 100 ml of methanol. The filtrate was then concentrated to about half, and approximately the same amount of warm water was added to it to precipitate the N-(D)-ribitylxylidine (I). Cooling and stirring for 3 hours in an icewater bath was followed by filtration with suction, and the crystals were washed with water and cold (0°–5° C.) methanol and dried at 70° C. under reduced pressure.

EXAMPLES 1 AND 2, COMPARATIVE EXAMPLE 1

A. Reaction with pure crystalline ribose

In each case 40.0 g (0.267 mol) of D-ribose (II) were weighed out and made up to 360 ml with methanol as a ribose solution, and 32.9 g (0.272 mol) of 3,4-dimethylaniline (III) in 150 ml of methanol were used.

TABLE 1

| Example | Weight of III [g (mol)] | Boric acid added [mg] | Weight of I [g] | Ribitylxylidine (I) Yield of I [% of theory] | Angle of rotation $[\alpha_D^{25}$ (in 2 M HCl)] |
|---|---|---|---|---|---|
| 1 | 32.9 (0.272) | 150 | 61.0 | 89.6 | −37.5°(c = 1.398) |
| 2 | 32.9 (0.272) | 150 | 60.7 | 89.2 | −36.5°(c = 1.37) |
| Comp. 1 | 32.9 (0.272) | — | 37.5 | 55.1 | −37.0°(c = 1.095) |

EXAMPLE 3

The procedure of Examples 1 and 2 was followed, except that the reaction conditions were not 2 h at 5 bar hydrogen pressure but 2 h at 0.5 bar hydrogen pressure, affording the N-(D)-ribitylxylidine in a yield of 86% of theory in a purity of about 90% (m.p.=133° C.; $[\alpha]_D^{25}=-32.1$).

EXAMPLE 4

The procedure of Examples 1 and 2 was followed, except that the reaction conditions were not 2 h at 5 bar hydrogen pressure but 2 h at 1.5 bar hydrogen pressure, affording the N-(D)-ribitylxylidine in a yield of 85% of theory (m.p.=136° C./$[\alpha]_D^{25}=-34.2$).

EXAMPLES 5 TO 7 AND COMPARATIVE EXAMPLES 2 TO 4

B. Reaction with a ribose solution prepared by weighing out the amount shown in Table 2 of a ribose which was, inter alia, 64.6% by weight ribose and 30.1% by weight water, making up to 360 ml with methanol.

TABLE 2

| Example | Weight of II [g (mol)] | | Weight of III [g] | Boric acid added [mg] | Weight of I [g] | Ribitylxylidine (I) Yield of I [% of theory] | Purity of I [HPLC] |
|---|---|---|---|---|---|---|---|
| Comp. 2 | 60.3 | (0.260) | 33.0 g | — | 34.8 | 52.5% | 99.4% |
| Comp. 3 | 61.54 | (0.265) | 33.6 g | — | 33.6 | 50.7% | 99.2% |
| Comp. 4* | 61.54 | (0.265) | 33.6 g | — | 40.6 | 61.2%* | 99.4% |
| 5 | 61.54 | (0.265) | 33.6 g | 150 | 58.8 | 88.7% | 99.6% |
| 6 | 61.54 | (0.265) | 33.6 g | 150 | 60.5 | 91.3% | 99.8% |
| 7 | 61.54 | (0.265) | 33.6 g | 150 | 59.6 | 89.9% | 99.5% |

*denotes stirring for 9 h (instead of 2 h) at 55° C. and 5 bar $H_2$.

EXAMPLES 8 TO 15 AND COMPARATIVE EXAMPLES 5 TO 11

Ribitylxylidine yield as a function of amount of boric acid added

C. Reaction with a ribose solution prepared by weighing out in each case 75.5 g of crude ribose having a ribose content of 47.5% by weight (corresponding to 35.86 g (0.239 mol); total reducing sugar content: 67% by weight), which was obtained from arabinose as described in German Laid-Open Application DOS No. 3,004,304.

| Example | Weight of III [g] | Boric acid added [mg] | (mmol/mol II) | Ribitylxylidine Weight [g] | Yield [% of theory] |
|---|---|---|---|---|---|
| Comp. 5 | 35.5 (0.293 mol) | — | — | 37.2 | 61.0% |
| Comp. 6 | 35.5 | — | — | 37.3 | 61.2% |
| Comp. 7 | 35.5 | 10 | (0.68) | 40.0 | 65.6% |
| Comp. 8 | 35.5 | 20 | (1.36) | 41.4 | 67.9% |
| Comp. 9 | 35.5 | 50 | (3.39) | 48.6 | 79.7% |
| 8 | 35.5 | 100 | (6.78) | 51.3 | 84.2% |
| 9 | 35.5 | 100 | (6.78) | 52.8 | 86.6% |
| 10 | 35.5 | 100 | (6.78) | 52.4 | 86.0% |
| 11 | 35.5 | 150 | (10.17) | 53.0 | 87.0% |
| 12 | 35.5 | 150 | (10.17) | 52.6 | 86.3% |
| 13 | 35.5 | 200 | (13.57) | 53.2 | 87.3% |
| 14 | 35.5 | 300 | (20.34) | 51.7 | 84.8% |
| 15 | 35.5 | 400 | (27.14) | 48.0 | 78.8% |
| Comp. 10 | 35.5 | 700 | (47.48) | 47.2 | 77.4% |
| Comp. 11 | 35.5 | 1200 | (81.0) | 46.5 | 76.3% |

EXAMPLE 16

Reaction starting from 3,4-dimethyl-1-nitrobenzene 40.32 g (266.6 mmol) of 3,4-dimethyl-1-nitrobenzene and 22 g of Raney nickel were hydrogenated in 200 ml of methanol at 55° C. and 5 bar of $H_2$ pressure for 2 h. According to analysis by gas chromatography, the hydrogenation to 3,4-dimethylaniline gave no byproducts. A further 22 g of Raney nickel were then added to the mixture. 40 g of 100% pure ribose and 1.0 g of boric acid, made up to 360 ml with methanol, were then pumped in over 4 h at 5 bar $H_2$ pressure at 55° C. The reaction mixture was maintained at 5 bar $H_2$ pressure and 55° C. for a further 2 h. The catalyst was then separated off at 60° C. on a hot suction filter. The mother liquor was concentrated to 350 g, and 350 g of hot water were then added. The reaction mixture obtained was cooled down and then stirred at room temperature for 1 h and in an ice-water bath for 3 h. The crystals obtained were filtered off with suction, washed with 50 ml each of cold water and cold methanol and dried. 58.5 g were obtained, corresponding to 86% of theory ($[\alpha]_D^{25} = -37.2$).

We claim:

1. A process for preparing N-(D)-ribitylxylidine, which comprises reacting D-ribose with 3,4-dimethylaniline or 3,4-dimethyl-1-nitrobenzene in aqueous or aqueous/organic solution or in solution in a water-soluble organic solvent under a hydrogen pressure of about 2 to 9 bar and a temperature of from about 40° to 80° C., and in the presence of a hydrogenation catalyst and a boric acid compound; and wherein said boric acid compound is used in a catalytic amount of from about 6–35 mmol, per mole of ribose.

2. The process as claimed in claim 1, wherein the boric acid compound used is boron oxide, a borate or boric acid itself.

3. The process as claimed in claim 1, wherein the reaction is carried out at from 50° to 60° C.

4. The process as claimed in claim 1, wherein the reaction is carried out in the presence of from 6 to 20 mmol of the boric acid compound per mole of ribose.

5. The process as claimed in claim 1, wherein the reaction is carried out at hydrogen pressures of from 2 to 5 bar.

6. The process as claimed in claim 1, wherein said aqueous/organic solution is a solution of water and a lower alkyl alcohol, and said water-soluble organic solvent is a lower alkyl alcohol.

* * * * *